(12) United States Patent
Hodge

(10) Patent No.: US 10,936,698 B2
(45) Date of Patent: Mar. 2, 2021

(54) SYSTEM AND METHOD FOR INTEGRATION OF TELEMEDICINE INTO MULTIMEDIA VIDEO VISITATION SYSTEMS IN CORRECTIONAL FACILITIES

(71) Applicant: **Global Tel*Link Corporation**, Reston, VA (US)

(72) Inventor: Stephen Hodge, Aubrey, TX (US)

(73) Assignee: **Global Tel*Link Corporation**, Reston, VA (US)

(*) Notice: Subject to any disclaimer, the term of this patent is extended or adjusted under 35 U.S.C. 154(b) by 1315 days.

(21) Appl. No.: 15/149,836

(22) Filed: May 9, 2016

(65) Prior Publication Data

US 2017/0323070 A1 Nov. 9, 2017

(51) Int. Cl.
| | | |
|---|---|---|
| *G16H 10/00* | (2018.01) | |
| *G06F 19/00* | (2018.01) | |
| *H04L 29/06* | (2006.01) | |
| *G16H 10/60* | (2018.01) | |
| *H04W 4/38* | (2018.01) | |
| *H04M 3/38* | (2006.01) | |

(Continued)

(52) U.S. Cl.
CPC ........ *G06F 19/3418* (2013.01); *A61B 5/0022* (2013.01); *G16H 10/60* (2018.01); *H04L 65/1066* (2013.01); *H04L 65/4015* (2013.01); *H04M 3/38* (2013.01); *H04W 4/38* (2018.02); *A61B 5/0077* (2013.01); *H04M 3/567* (2013.01); *H04M 2250/12* (2013.01)

(58) Field of Classification Search
CPC ... G06F 19/3418; G06F 16/951; G06F 19/321
See application file for complete search history.

(56) References Cited

U.S. PATENT DOCUMENTS 7,037,267 B1 5/2006 Lipson et al.
2005/0216310 A1 9/2005 Clements et al.
(Continued)

FOREIGN PATENT DOCUMENTS

EP 1659512 A2 5/2006
EP 2940612 A1 11/2015

OTHER PUBLICATIONS

International Search Report and Written Opinion directed to International Patent Application No. PCT/US2017/031731, dated Aug. 2, 2017; 17 pages.

(Continued)

*Primary Examiner* — Reginald R Reyes
(74) *Attorney, Agent, or Firm* — Sterne, Kessler, Goldstein & Fox P.L.L.C.

(57) ABSTRACT

A system and method for integration of telemedicine into multimedia video visitation systems of correctional facilities is disclosed herein. The system includes a telemedicine center that communicates with a medical center located at a correctional facility and a physician kiosk remote to the correctional facility. The medical center includes an inmate kiosk and a medical assistant station. The inmate kiosk and physician kiosk participate in a secure video call as part of an appointment between the inmate and physician. The inmate kiosk coordinates with the telemedicine center to verify an identity of the inmate. The inmate kiosk interfaces with a number of medical sensors and communicates data collected from the sensors to the physician kiosk.

14 Claims, 10 Drawing Sheets

(51) Int. Cl.
    *A61B 5/00*     (2006.01)
    *H04M 3/56*     (2006.01)

(56) References Cited

U.S. PATENT DOCUMENTS

| | | |
|---|---|---|
| 2006/0271400 A1 | 11/2006 | Clements et al. |
| 2007/0118389 A1 | 5/2007 | Shipon |
| 2009/0083066 A1 | 3/2009 | Bailey et al. |
| 2011/0202174 A1 | 8/2011 | Bogash et al. |
| 2011/0245967 A1* | 10/2011 | Shah ................ G07F 17/0092 |
| | | 700/236 |
| 2012/0029303 A1 | 2/2012 | Shaya |
| 2013/0060576 A1 | 3/2013 | Hamm et al. |
| 2014/0089001 A1 | 3/2014 | Macoviak et al. |
| 2014/0100858 A1* | 4/2014 | Grollmuss ............ G06Q 50/22 |
| | | 705/2 |
| 2015/0294079 A1 | 10/2015 | Bergougnan |
| 2015/0310183 A1 | 10/2015 | Madhavan et al. |
| 2016/0055307 A1 | 2/2016 | Macoviak et al. |
| 2019/0096534 A1* | 3/2019 | Joao .................. G16H 15/00 |

OTHER PUBLICATIONS

International Search Report and Written Opinion directed to International Patent Application No. PCT/US2017/029398, dated Jul. 26, 2017; 12 pages.

Supplementary European Search Report and opinion directed to related European Application No. EP 17796685.0, dated Dec. 12, 2019; 10 pages.

\* cited by examiner

SYSTEM AND METHOD FOR INTEGRATION OF TELEMEDICINE INTO MULTIMEDIA VIDEO VISITATION SYSTEMS IN CORRECTIONAL FACILITIES

BACKGROUND

Field

The disclosure relates to telemedicine, and specifically the equipment and methods to integrate telemedicine into multimedia video visitation systems.

Background

Correctional facilities often do not employ full-time physicians, particularly specialists. Security concerns prevent inmates from visiting physicians outside of correctional facilities except during emergencies. Thus, physicians visit correctional facilities periodically or as needed. Physical visits to facilities, by their very nature, prevent simultaneous visits to other facilities, resulting in reduced overall availability of medical expertise. Accordingly, a telemedicine system that enables remote consultation would increase overall physician availability for inmates in correctional facilities.

BRIEF DESCRIPTION OF THE DRAWINGS/FIGURES

The accompanying drawings, which are incorporated herein and form a part of the specification, illustrate embodiments of the present disclosure and, together with the description, further serve to explain the principles of the disclosure and to enable a person skilled in the pertinent art to make and use the embodiments.

Figure 1:
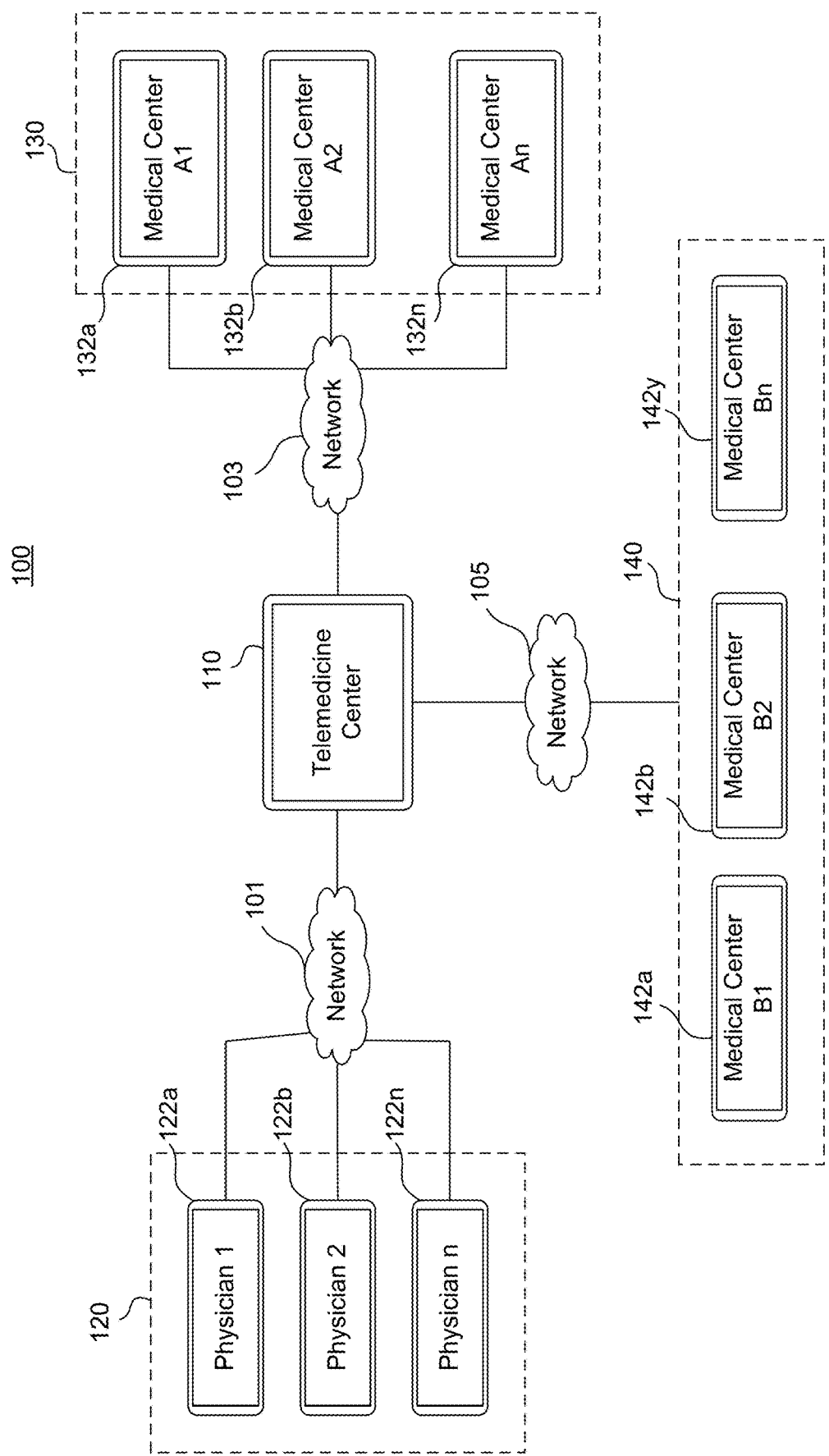
FIG. 1 illustrates a block diagram of a telemedicine system, according to exemplary embodiments of the present disclosure.

The present disclosure will be described with reference to the accompanying drawings. In the drawings, like reference numbers indicate identical or functionally similar elements. Additionally, the left most digit(s) of a reference number identifies the drawing in which the reference number first appears.

DETAILED DESCRIPTION

The following Detailed Description refers to accompanying drawings to illustrate exemplary embodiments consistent with the disclosure. References in the Detailed Description to "one exemplary embodiment," "an exemplary embodiment," "an example exemplary embodiment," etc., indicate that the exemplary embodiment described may include a particular feature, structure, or characteristic, but every exemplary embodiment may not necessarily include the particular feature, structure, or characteristic. Moreover, such phrases are not necessarily referring to the same exemplary embodiment. Further, when a particular feature, structure, or characteristic is described in connection with an exemplary embodiment, it is within the knowledge of those skilled in the relevant art(s) to affect such feature, structure, or characteristic in connection with other exemplary embodiments whether or not explicitly described.

The exemplary embodiments described herein are provided for illustrative purposes, and are not limiting. Other exemplary embodiments are possible, and modifications may be made to the exemplary embodiments within the spirit and scope of the disclosure. Therefore, the Detailed Description is not meant to limit the invention. Rather, the scope of the invention is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc. Further, any of the implementation variations may be carried out by a general purpose computer, as described below.

For purposes of this discussion, any reference to the term "module" shall be understood to include at least one of software, firmware, and hardware (such as one or more circuit, microchip, or device, or any combination thereof), and any combination thereof. In addition, it will be understood that each module may include one, or more than one, component within an actual device, and each component that forms a part of the described module may function either cooperatively or independently of any other component forming a part of the module. Conversely, multiple modules described herein may represent a single component within an actual device. Further, components within a module may be in a single device or distributed among multiple devices in a wired or wireless manner.

The following Detailed Description of the exemplary embodiments will so fully reveal the general nature of the invention that others can, by applying knowledge of those skilled in relevant art(s), readily modify and/or adapt for various applications such exemplary embodiments, without undue experimentation, without departing from the spirit and scope of the disclosure. Therefore, such adaptations and modifications are intended to be within the meaning and plurality of equivalents of the exemplary embodiments based upon the teaching and guidance presented herein. It is to be understood that the phraseology or terminology herein is for the purpose of description and not of limitation, such that the terminology or phraseology of the present specification is to be interpreted by those skilled in relevant art(s) in light of the teachings herein.

Overview

Correctional facilities often do not have full-time physicians on site to tend to the medical needs of inmates. Instead, physicians may make rounds at multiple facilities, visiting each one for a specified duration of time. The sparse availability of physicians in correctional facilities may complicate appointment scheduling and reduce urgent care availability. For example, a doctor visiting a facility for three days per month might meet with only thirty patients during that time. Those appointments could be booked months in advance. In facilities that do employ in-house physicians, those physicians are often generalists—specialists only visit the facilities sporadically.

Correctional facilities often employ local medical assistants, such as physician assistants, registered nurses, or medical technicians, to assist with medical issues. Similar to medical assistants outside of correctional facilities, local medical assistants are stationed at the correctional facility to assist physicians in performing check-ups such as obtaining and recording situations surrounding a medical condition, and obtaining inmate vital signs, and/or following up on previous treatments or conditions. When physicians prescribe medications, local medical assistants additionally assist in distributing medications to an appropriate dispenser for an inmate to retrieve the medication and/or in administering medications to inmates.

Education programs such as health seminars led by physicians are typically conducted in person. A physician may conduct the same seminar—for example, a seminar on substance abuse—at multiple facilities by traveling to the various facilities and conducting the seminars on different days and times. Multiple instances of a given seminar increase costs to the facilities and may reduce the amount of time a physician has for appointments with individual inmates. Playing a recorded seminar at multiple facilities does not allow for inmate-physician interaction.

Medications are dispensed at correctional facilities to treat both physical and mental illnesses such as infections, pain, and depression, as well as help prevent the spread of diseases. However, inmates that have access to such medications may use them improperly, such as by selling, trading to gain favors with other inmates, improperly administering the medications, facilitating addictions. To obtain medications, inmates may attempt to unduly influence local medical assistants by way of manipulation, falsehoods, and/or duress.

In light of the above, the present disclosure provides a system and method for a secure telemedicine system whereby physicians can participate in medical appointments or seminars at multiple facilities using a multimedia video visitation framework. The framework includes a plurality of medical sensors as well as a remote drug dispensing unit.

Telemedicine System

FIG. 1 illustrates a block diagram of a telemedicine system 100, according to exemplary embodiments of the present disclosure. The telemedicine system 100 includes a telemedicine center 110 configured to communicate with a variety of devices over a variety of different communication networks. In particular, the telemedicine center 110 is configured to communicate with a physician center 120, a first medical center 130, and a second medical center 140. As will be further explained below, the telemedicine center 110 receives/transmits medical data, identification data, and scheduling data from/to the physician center 120, the first medical center 130, and the second medical center 140. To communicate with the physician center 120, the telemedicine center 110 interfaces with a network 101. The network 101 may be any one or more of a public switched telephone network (PSTN), a wide area network (WAN), or the Internet. To communicate with the first medical center 130, the telemedicine center 110 interfaces with a network 103. The network 103 may be any one or more of a PSTN, a local area network (LAN), a WAN, or the Internet. To communicate with the second medical center 140, the telemedicine center 110 interfaces with a network 105. The network 105 may be any one or more of a public switched telephone network (PSTN), a WAN, or the Internet. Communication on networks 101, 103, 105 is protected using the 256-bit-key Triple Data Encryption Standard (3DES), or equivalent, that is also employed for inmate communications subject to attorney-client privilege. This encryption protects patient privacy according to the Health Insurance Portability and Accountability Act of 1996 (HIPAA).

The physician center 120 is a location remote to a correctional facility that includes a physician, physician assistant, or nurse practitioner, etc. The physician center 120 may be configured to include any number of physician kiosks 122a-122n for communicating with the telemedicine center 110. Each of the physician kiosks 122a-122n are configured to transmit medical data such as a request for medication, patient data, billing data, etc. Each of the physician kiosks 122a-122n may include one or more devices such as a computer, a tablet, a scanner, a facsimile machine, etc. Further, the physician kiosks 122a-122n can be located at one location or any number of locations. For example, physician kiosk 122a may be located in Washington and physician kiosk 122b may be located in Missouri. Further examples and explanations of the physician kiosks 122a-122n will be in reference to the physician center 120.

The first medical center 130 is a medical area provided at a first correctional facility. The first medical center 130 may include any number of patient centers 132a-132n. Each of the patient centers 132a-132n is configured to engage in a video call with one or more patient centers, receive medical data, facilitate distribution of medication, and perform identity verification of inmates and local medical assistants. Further examples and explanations of the patient centers 132a-132n will be in reference to the first medical center 130. As will be explained in further detail below, the first medical center 130 includes station(s) and dispenser(s) for receiving, preparing, and dispensing medication remotely from the prescribing physician.

The second medical center 140 is a medical area provided at a second correctional facility distinct from the first correctional facility. The second medical center 140 may include any number of patient centers 142a-142n. Each of the patient centers 142a-142n is configured to engage in a video call with a physician kiosk, receive medical data, facilitate distribution of medication, and perform identity verification of inmates and local medical assistants. Further examples and explanations of the patient centers 142a-142n will be in reference to the second medical center 140. As will be explained in further detail below, the second medical center 140 includes station(s) and dispenser(s) for distributing and dispensing medication remotely from the prescribing physician.

A telemedicine appointment or consultation involves connecting a physician kiosk, (e.g., physician kiosk 122a) and a patient center (e.g. patient center 132b) via a video call facilitated by telemedicine center 110. In an embodiment, the identities of both the physician and inmate are separately verified prior to the call at their respective centers 120, 130 in conjunction with the telemedicine center 110. The physician and inmate interact via video and voice and, with the assistance of a medical assistant collocated with the inmate, the physician examines the inmate as necessary. Before, during, and/or after the call, medical data is gathered from sensors deployed at the patient center 132b and transmitted to the physician kiosk 122a via telemedicine center 110. The medical data is organized and displayed in real-time at physician kiosk 122a along with other information pertinent to the interaction. In various embodiments, the physician kiosk 122a allows a physician to control the sensors collocated with the inmate. In some embodiments, the physician kiosk 122a also allows for remote medication dispensation controlled by the physician. Thus, in various embodiments, the telemedicine center 110 facilitates a physician-inmate consultation by relaying video call and sensor data between physician kiosks and patient centers.

A seminar involves connecting a physician kiosk (e.g. physician kiosk 122a) and one or more patient centers (e.g. patient centers 132b and 142b) via a group video call facilitated by telemedicine center 100. In some embodiments, the physician and inmates at the various patient centers interact via video and voice to communicate health information to inmates at different facilities.

Telemedicine Center

Figure 2:
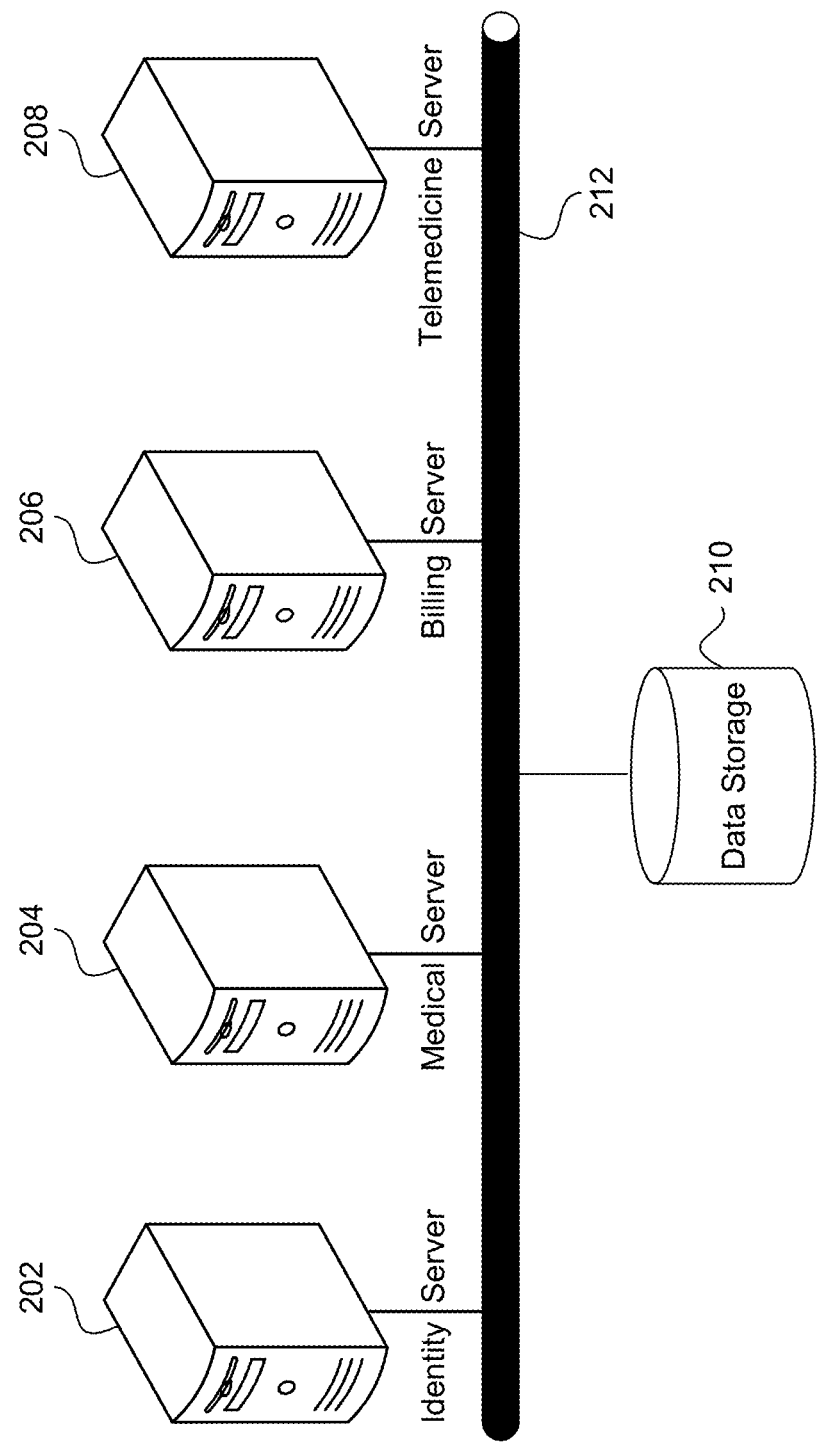
FIG. 2 illustrates a block diagram of a telemedicine center, according to exemplary embodiments of the present disclosure.

FIG. 2 illustrates a block diagram of a telemedicine center 200, according to exemplary embodiments of the present disclosure. The telemedicine center 200 is an exemplary embodiment of the telemedicine center 110 of FIG. 1. The telemedicine center 200 includes an identity server 202, a medical server 204, a billing server 206, a telemedicine server 208, and data storage 210, that are all connected to each other via a network bus 212.

In an embodiment, each of the servers 202-208 is constructed as a distinct physical hardware device. In another embodiment, each of the servers 202-208 is a virtual server contained in one or more distinct physical hardware devices. The number of physical hardware machines can be scaled to match the number of simultaneous user connections desired to be supported in a telemedicine system such as the telemedicine system 100.

The identity server 202 consists of any number of servers, and is configured to store and organize identity data. The identity data includes data relating to physicians, inmates, and local medical assistants. The identity data includes such data as names, biometric data, and contact data of physicians, inmates, and local medical assistants allowed to access the telemedicine system. In an embodiment, the identity data also includes data related to the physician kiosks 122a-122n such as make and model of the devices and contact information, and/or data related to equipment from a correctional facility used to connect to the telemedicine system.

The medical server 204 also consists of any number of servers, and is configured to securely receive, organize, and transmit medical data. In essence, the medical server 204 is configured to receive medical data such as vitals (e.g., blood pressure, heart rate, oxygen saturation), a request for medication data, medication fulfillment data, check-up data, medical questionnaires, etc., and to securely store the data. In an embodiment, the medical server 204 is configured to organize the medical data such that when the medical data is received it is tagged and linked to a corresponding physician, inmate, and/or local medical assistant, to facilitate searching the medical data. The medical server 204 is also configured to share some or all of the stored medical data within the telemedicine center and also with personnel such as physicians or local medical assistants, based on authorization. For example, a local medical assistant may only have access to a list of available prescriptions for an inmate while another local medical assistant or a physician may have access to all medical data of the same inmate.

The billing server 206 consists of any number of servers, and is configured to securely receive, organize, and transmit billing and accounting data. In detail, the billing server 206 stores data relating to billing for an inmate. Embodiments of the billing data include responsible billing parties or historical costs of medications. When the billing data is received, the received data is tagged and linked to a corresponding physician, inmate, and/or local medical assistant to facilitate searching the billing data. Similar to the medical server 204, the billing server 206 is also configured to share some or all of the stored data within the telemedicine center and also with personnel such as physicians or local medical assistants, based on authorization.

The telemedicine server 208 consists of any number of servers, and is configured to schedule and track appointments as well as the distribution of medications within the telemedicine system 100. The telemedicine server 208 communicates with the physician center 120 and/or the medical centers 130, 140 to schedule and coordinate appointments and distribution of a medication. For example, the telemedicine server 208 communicates with the physician center 120 to determine whether to distribute medication to a particular inmate. As another example, the telemedicine server 208 communicates with the medical centers 130, 140 to coordinate dispensation of medication.

To facilitate the scheduling of appointments, the telemedicine server 208 maintains a schedule of appointments between physicians and inmates. In an embodiment, the schedule is stored in data storage 210. Embodiments of data stored in a schedule include an identification of a physician, an identification of an inmate, a time and date for an appointment, an identity of a physician kiosk, or an identity of an inmate kiosk. Storage of kiosk identities ensures that kiosks are available for inmates and physicians at the time of the appointment. In other embodiments, schedules for particular kiosks are stored and maintained by the respective kiosks.

To facilitate the scheduling of medication distribution, the telemedicine server 208 communicates with the identity server 202, the medical server 204, and the billing server 206. The telemedicine server 208 retrieves data gathered and stored by these servers and uses the data for such actions as validating an identity of a person making a request for medication and generating a schedule to distribute the medication. For example, after a request for medication has been received from the first medical center 130, the telemedicine server 208 can confirm an identity of a local medical assistant that submitted the request based on a comparison of identity verification data received with the request for medication with identity data stored on the identity server 202. To schedule the distribution of medication, the telemedicine server 204 can retrieve medication data stored by the medical server 204 to determine when to distribute medication, to provide an example.

In embodiments, the data storage 210 is a primary storage for the servers 202-208. In other embodiments, the data storage 210 is a back-up storage for servers 202-208. Further, because the data stored on the data storage 210 may consume significant amounts of storage space, embodiments of the data storage 210 include a Network Attached Storage (NAS) device configured as a mass storage device. To conserve space and preserve longevity, the data storage 210 preferably includes a backup routine to transfer data to permanent storage devices, such as archival permanent storage or optical disks, after a predetermined time has elapsed since the initial recording of that data. The storage device 210 is connected to identity server 202, the medical server 204, the billing server 206, and the telemedicine server 208 by way of the network bus 212.

Figure 3:
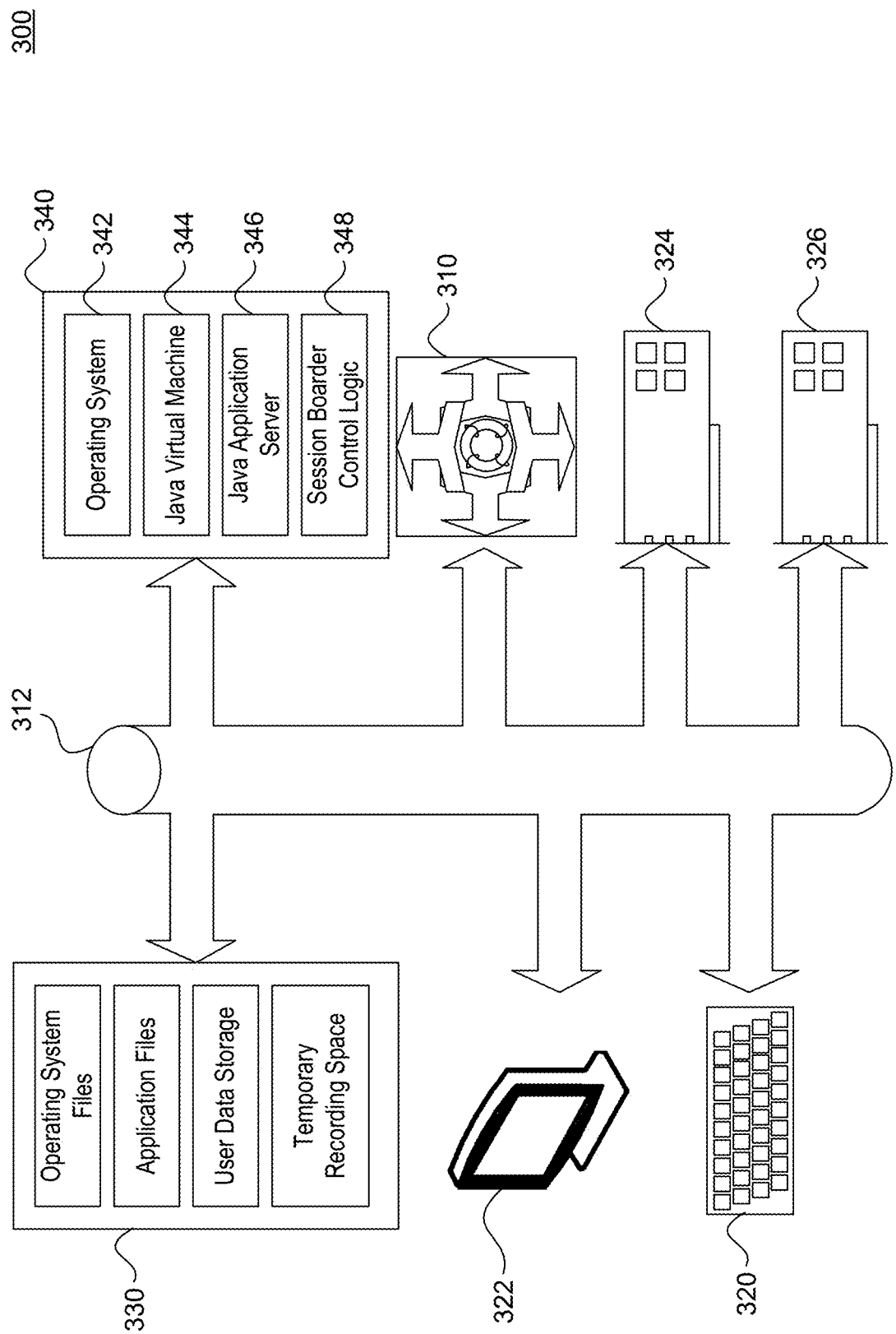
FIG. 3 illustrates a block diagram of a telemedicine server according to exemplary embodiments of the present disclosure.

FIG. 3 illustrates a block diagram of a telemedicine server 300, according to exemplary embodiments of the present disclosure. The telemedicine server 300 represents an exemplary embodiment of the telemedicine server 208 depicted in FIG. 2. The telemedicine server 300 functions as the primary logic processing center in the telemedicine system 100. The telemedicine server 300 includes one or more central processing units (CPUs) 310 connected via a bus 312 to several other peripherals. Such peripherals include an input device, such as a keyboard and/or mouse 320, a monitor 322 for displaying information, a network interface card 324 and/or a modem 326 that provide network connectivity and communication.

The telemedicine server 300 also includes internal data storage 330. The data storage 330 is non-volatile storage, such as one or more magnetic hard disk drives (HDDs) and/or one or more solid state drives (SSDs). The data storage 330 is used to store a variety of important files, documents, or other digital information, such as the operating system files, application files, user data, and/or temporary recording space.

The telemedicine server 300 also includes system memory 340. The system memory 340 is preferably faster and more efficient than the data storage 330, and is configured as random access memory (RAM) in an embodiment. The system memory 340 contains the runtime environment of the application server, storing temporary data for any of the operating system 342, java virtual machine 344, java application server 346, and telemedicine control logic 348.

Medical Center

Figure 4:
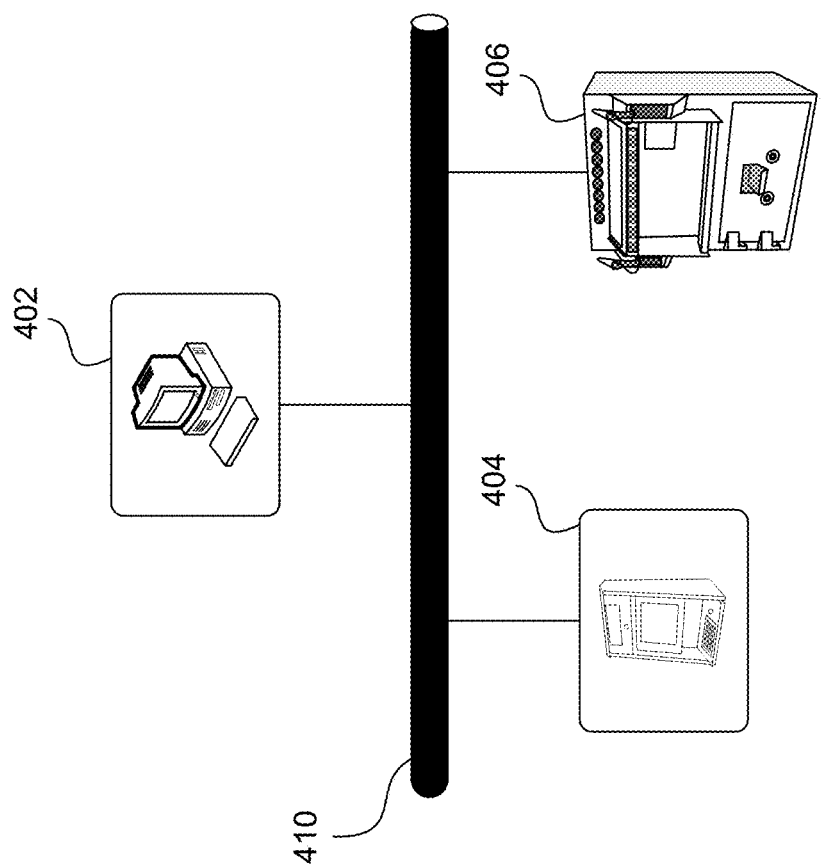
FIG. 4 illustrates a block diagram of a medical center according to exemplary embodiments of the present disclosure.

FIG. 4 illustrates a block diagram of a medical center 400, according to exemplary embodiments of the present disclosure. The medical center 400 is an exemplary embodiment of one of the patient kiosks 132a-132n, 142a-142n of FIG. 1. The medical center 400 includes a medical assistant station 402, an inmate kiosk 404, and a medication dispenser 406, that are all connected to each other via a network bus 410.

The medical assistant station 402 is configured to function as a data reviewing center for any local medical assistants stationed at a correctional facility. The medical assistant station 402 may include a computer, tablet, or phone capable of viewing medical data. By way of the medical assistant station 402, a medical assistant may access inmate data such as the medical data from the medical server 204, the billing data from the billing server 206, and/or the scheduling and tracking data from the telemedicine server 208. The medical assistant station 402 is also configured to verify an identity of a medical assistant. Verification of a medical assistant's identity may be performed by use of one or more of logon information, a keycard, or biometric data.

The inmate kiosk 404 is configured to function as a data reviewing center for an inmate at a correctional facility. The inmate kiosk 404 may include a computer, tablet, or phone capable of viewing medical data. By way of the inmate kiosk 404, an inmate may have access to his/her medical data such as the medical data from the medical server 204, the billing data from the billing server 206, and/or the scheduling and tracking data from the telemedicine server 208. The inmate kiosk 404 is also configured to verify an identity of an inmate. Verification of an inmate's identity may be performed by use of one or more of logon information, a key card, or biometric data.

The medication dispensing station 406 includes a device configured to receive medication and, after verifications are performed, to dispense the medication through a retrieval bin or other retrieval apparatus. The medication dispensing station 406 may be a standalone device, meaning that all identity verifications are performed remote to the medication dispensing station 406, or, as described in detail below, may be integrated with a verification station(s) such as the inmate kiosk 404. The medication dispensing station is configured to receive prescription data, including a patient identity and a medication name, and dispense the medication only after matching the identity of an inmate attempting to use the medication dispensing station with the patient identity provided to the medication dispensing station. In some embodiments, the medication dispensing station 406 only dispenses medication after also receiving authorization from telemedicine server 110.

Figure 5:
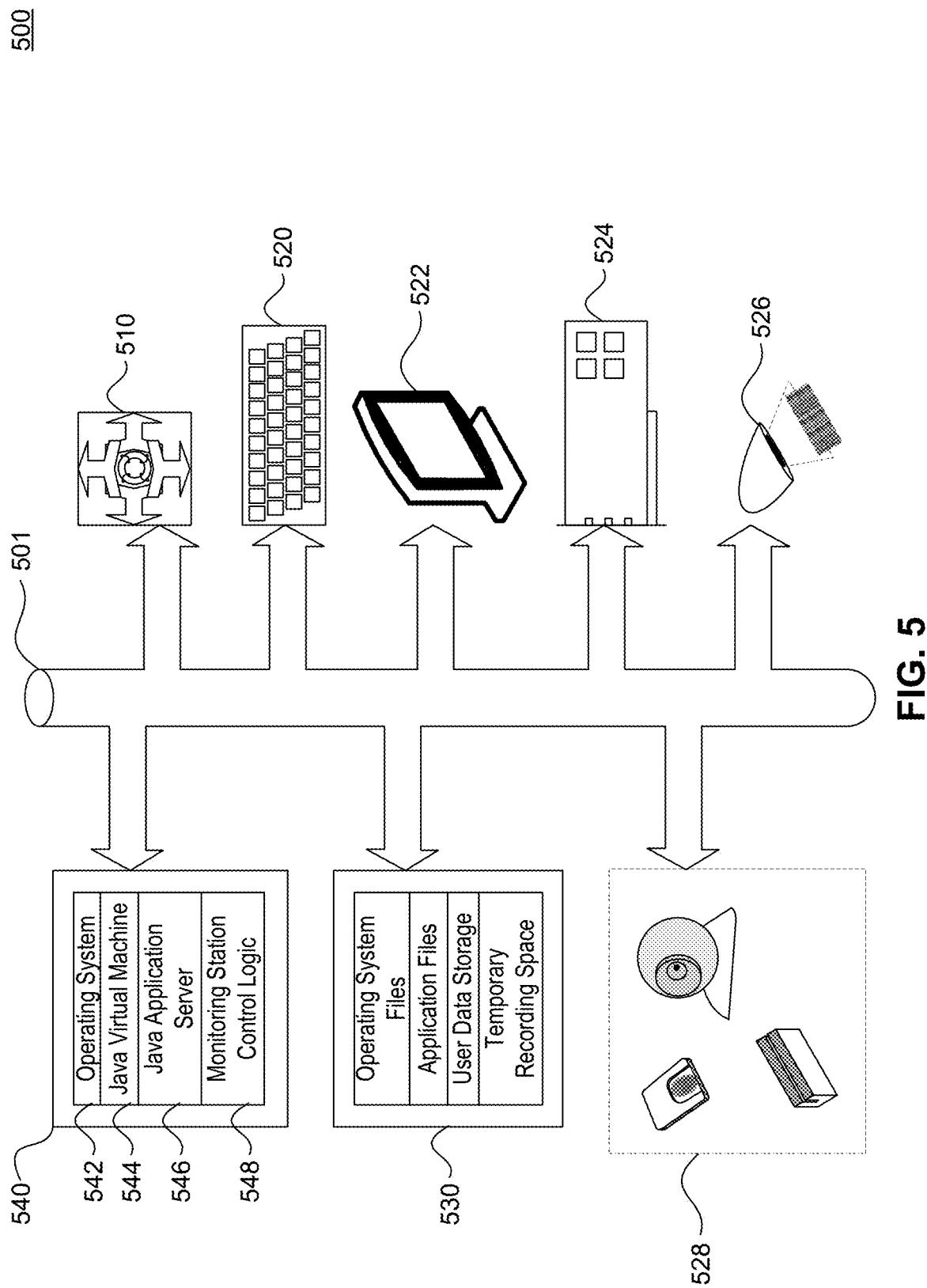
FIG. 5 illustrates a block diagram of a medication dispenser according to exemplary embodiments of the present disclosure.

FIG. 5 illustrates a block diagram of a medication dispensing station 500, according to exemplary embodiments of the present disclosure. The medication dispensing station 500 represents an exemplary embodiment of the electrical components of the medication dispensing station 406 depicted in FIG. 4. The medication dispensing station 500 includes one or more central processing units (CPU) 510 connected via a bus 501 to several other peripherals. Such peripherals include an input device, such as a keyboard and/or mouse 520, a monitor 522 for displaying information, a network interface card and/or modem 524 that provide network connectivity and communication with the medical center 400, a medication scanner 526 such as a barcode reader or an RFID reader for scanning medication. In some embodiments, the medication scanner 526 is incorporated internally within a medication dispensing device such that when medication is loaded or prior to being dispensed, the medication is scanned for verification purposes. In other embodiments, the medication scanner 526 is externally attached to the medication dispensing device so as to facilitate a medical assistant in scanning medication when loaded or dispensed. Peripherals for the medication dispensing station 500 further include an identification verification device 528 such a keycard reader or a biometric reader for verifying an identity of a medical assistant and/or an inmate.

The medication dispensing station 500 also includes internal data storage 530. The data storage 530 is non-volatile storage, such as one or more magnetic hard disk drives (HDDs) and/or one or more solid state drives (SSDs). The data storage 530 is used to store a variety of important files, documents, or other digital information, such as the operating system files, application files, user data, and/or temporary recording space.

The medication dispensing station 500 further includes system memory 540. The system memory 540 is preferably faster and more efficient than the data storage 530, and is configured as random access memory (RAM) in an embodiment. The system memory 540 contains the runtime environment of the application server, storing temporary data for any of the operating system 542, java virtual machine 544, java application server 546, and dispenser control logic 548.

Inmate Kiosk

Figure 6:
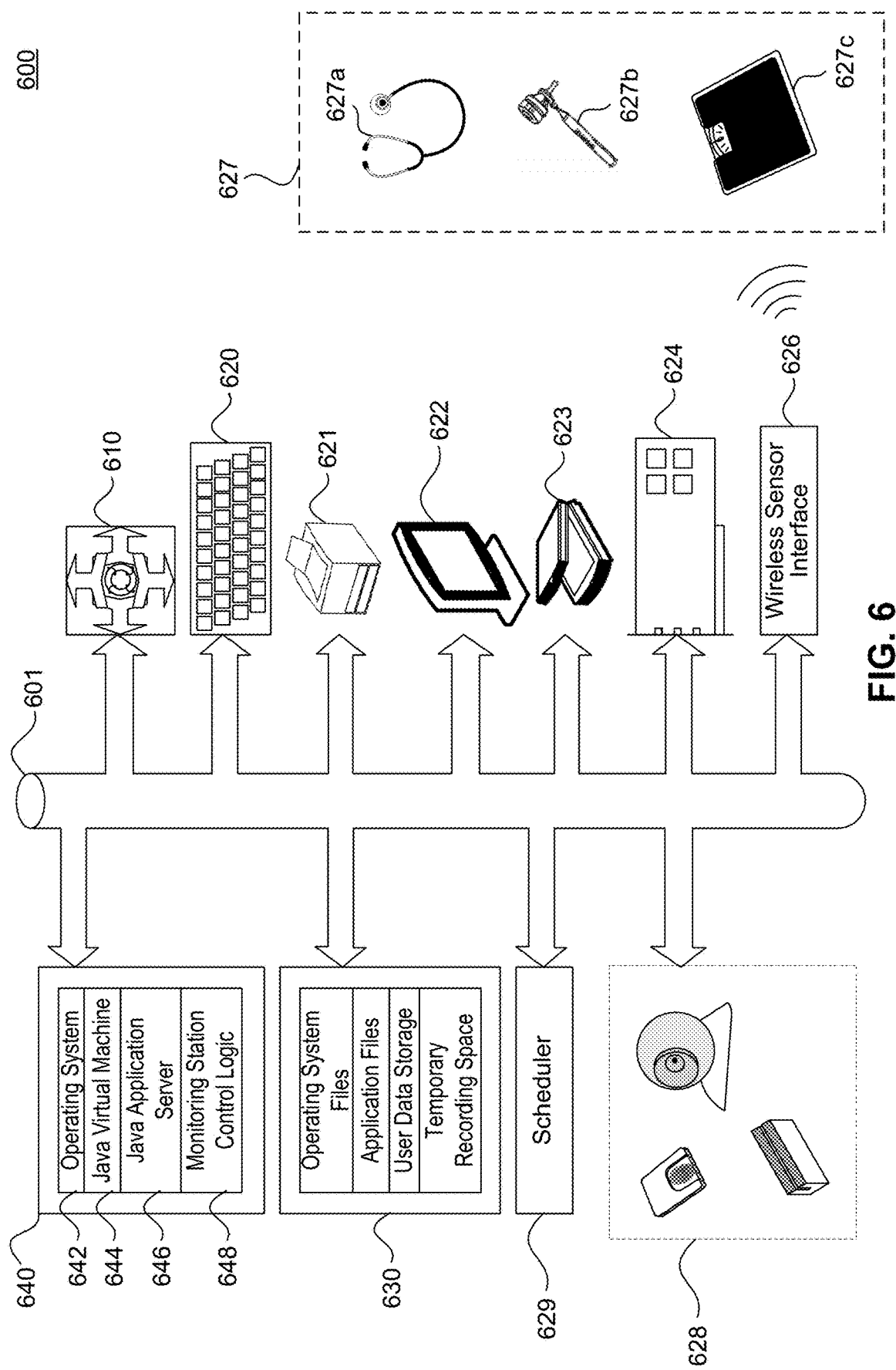
FIG. 6 illustrates a block diagram of an inmate kiosk according to exemplary embodiments of the present disclosure.

FIG. 6 illustrates a block diagram of an inmate kiosk 600, according to exemplary embodiments of the present disclosure. The inmate kiosk 600 is an exemplary embodiment of the electrical components of the inmate kiosk 404 depicted in FIG. 4. The inmate kiosk 600 includes one or more central processing units (CPU) 610 connected via a bus 601 to several other peripherals. Such peripherals include an input device, such as a keyboard and/or mouse 620, a display device such as monitor 622 for displaying information, a network interface card and/or modem 624 that provide network connectivity and communication with the medical center 400, printer 621 for printing medical information and images, scanner 623 for scanning medical information and images, and a wireless sensor interface 626 such as an RF transceiver for interfacing with wireless medical sensors 627 in proximity to the inmate kiosk 600.

The wireless sensor interface 626 employs one or more wireless communication protocols to interface with wireless medical sensors 627. Wireless medical sensors 627 include stethoscope 627a, wand camera probe 627b for viewing a patient's throat, nose, or ear canal, and scale 627b. Wireless medical sensors 627 may include other sensors not illustrated in FIG. 6, including an oxygen sensor, Breathalyzer, ultrasound, temperature sensor, EKG probes, blood pressure monitor, pulse rate monitor, DNA collector, or a point of care mobile analysis device for blood and urine analysis. In some embodiments inmate kiosk 600 includes a cardiac arrest unit for operation by the medical assistant under the guidance of the remote physician. Peripherals for the inmate kiosk 600 further include an identification verification device 628 such a keycard reader or a biometric reader for verifying an identity of a medical assistant and/or an inmate. In some embodiments, an image capture device such as a camera is used to capture video images used for a video call, and can also be used as identification verification device 628. In other embodiments, an image capture device used for a video call is distinct from an image capture device used as identification verification device 628. For example, the image capture device used as identification verification device 628 can be a three-dimensional (3D) camera used to capture and identify facial structure for biometric verification purposes.

The inmate kiosk 600 further includes a scheduling module 629 that communicates with the telemedicine server 208 for scheduling appointments utilizing the inmate kiosk 600. In embodiments where inmate kiosk 600 coordinates and maintains its own schedule, scheduling module 629 communicates scheduling requests to telemedicine server 208 for coordination with a physician and a physician kiosk.

The inmate kiosk 600 also includes internal data storage 630. The data storage 630 is non-volatile storage, such as one or more magnetic hard disk drives (HDDs) and/or one or more solid state drives (SSDs). The data storage 630 is used to store a variety of important files, documents, or other digital information, such as the operating system files, application files, user data, and/or temporary recording space.

The inmate kiosk 600 further includes system memory 640. The system memory 640 is preferably faster and more efficient than the data storage 630, and is configured as random access memory (RAM) in an embodiment. The system memory 640 contains the runtime environment of the application server, storing temporary data for any of the operating system 642, java virtual machine 644, java application server 646, and dispenser control logic 648.

The CPU 610 is configured to centrally control the inmate kiosk 600. For example, the CPU 610 establishes a secure video call connection with a physician kiosk by responding to a call request from the telemedicine center 110 or a user input to the kiosk. Once the connection is established, incoming video call data is received by the network interface card and/or modem 624 and processed by CPU 610, which sends the processed video call data to display device 622. In some embodiments, display device 622 also includes an audio output device such as a speaker. The image capture device captures video call data, the CPU 610 processes the outgoing video call data and delivers the outgoing video call data to the telemedicine center 110 via network interface card and/or modem 624. When wireless sensor interface 626 captures sensor data from sensors 627, the CPU 610 processes the sensor data and delivers the sensor data to the telemedicine center 110 via network interface card and/or modem 624.

Physician Kiosk

Figure 7:
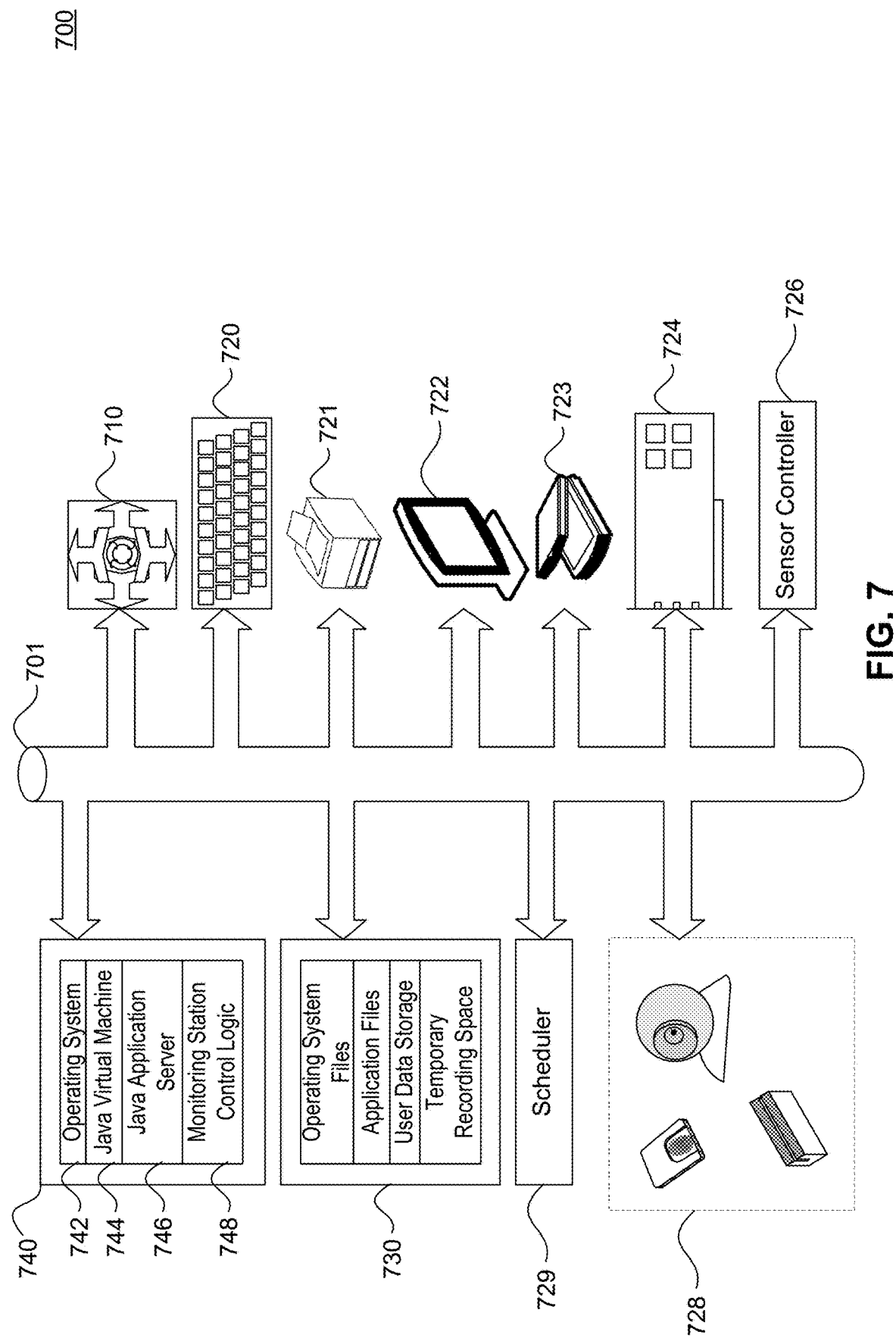
FIG. 7 illustrates a block diagram of a physician kiosk according to exemplary embodiments of the present disclosure.

FIG. 7 illustrates a block diagram of a physician kiosk 700, according to exemplary embodiments of the present disclosure. The physician kiosk 700 is an exemplary embodiment of the electrical components of the physician kiosks 122a-122n depicted in FIG. 1. The physician kiosk 700 includes one or more central processing units (CPUs) 710 connected via a bus 701 to several other peripherals. Such peripherals include an input device, such as a keyboard and/or mouse 720, a display device such as monitor 722 for displaying information, a network interface card and/or modem 724 that provide network connectivity and communication with the telemedicine center 110, printer 721 for printing medical information and images, scanner 723 for scanning medical information and images, and a sensor controller 726.

In an exemplary embodiment, the sensor controller 726 controls sensors located in proximity to an inmate kiosk in communication with the physician kiosk 700. In an embodiment, the sensor controller instructs a sensor, such as a blood pressure monitor, to provide a reading to the proximal inmate kiosk 600, which obtains the reading and communicates it to physician kiosk 700. In the embodiment illustrated in FIGS. 1, 6, and 7, communication between the physician kiosk and the medical sensors utilizes physician kiosk network interface card and/or modem 724, network 101, telemedicine center 110, network 103, inmate kiosk network interface card and/or modem 624, and wireless sensor interface 626. In other embodiments, a physician assistant located at the medical center controls and operates the medical sensors without control by the physician kiosk.

Peripherals for the physician kiosk 700 further include an identification verification device 728 such a keycard reader or a biometric reader for verifying an identity of a medical assistant and/or an inmate. The inmate kiosk 700 further includes a scheduling module 729 that communicates with the telemedicine server 208 for scheduling appointments utilizing the physician kiosk 700.

The physician kiosk 700 also includes internal data storage 730. The data storage 730 is non-volatile storage, such as one or more magnetic hard disk drives (HDDs) and/or one or more solid state drives (SSDs). The data storage 730 is used to store a variety of important files, documents, or other digital information, such as the operating system files, application files, user data, and/or temporary recording space.

The physician kiosk 700 further includes system memory 740. The system memory 740 is preferably faster and more efficient than the data storage 730, and is configured as random access memory (RAM) in an embodiment. The system memory 740 contains the runtime environment of the application server, storing temporary data for any of the operating system 742, java virtual machine 744, java application server 746, and dispenser control logic 748.

The CPU 710 is configured to centrally control the physician kiosk 700. For example, the CPU 710 establishes a secure video call connection with one or more inmate kiosks by responding to a call request from the telemedicine center 110 or a user input to the physician kiosk. Once the connection is established, incoming video call data is received by the network interface card and/or modem 724 and processed by CPU 710, which sends the processed video call data to display device 722. In some embodiments, display device 722 also includes an audio output device such as a speaker. The image capture device captures video call data, the CPU 710 processes the outgoing video call data and delivers the outgoing video call data to the telemedicine center 110 via network interface card and/or modem 724. When the network interface card and/or modem 724 receives sensor data from telemedicine server 110, the CPU 710 processes the sensor data and outputs the sensor data to the display device 722. In some embodiments, the CPU is also configured to generate an invoice based on a visit with a patient, the invoice including a visit duration and services rendered. In such embodiments, the CPU delivers the invoice to the billing server 206.

Figure 8:
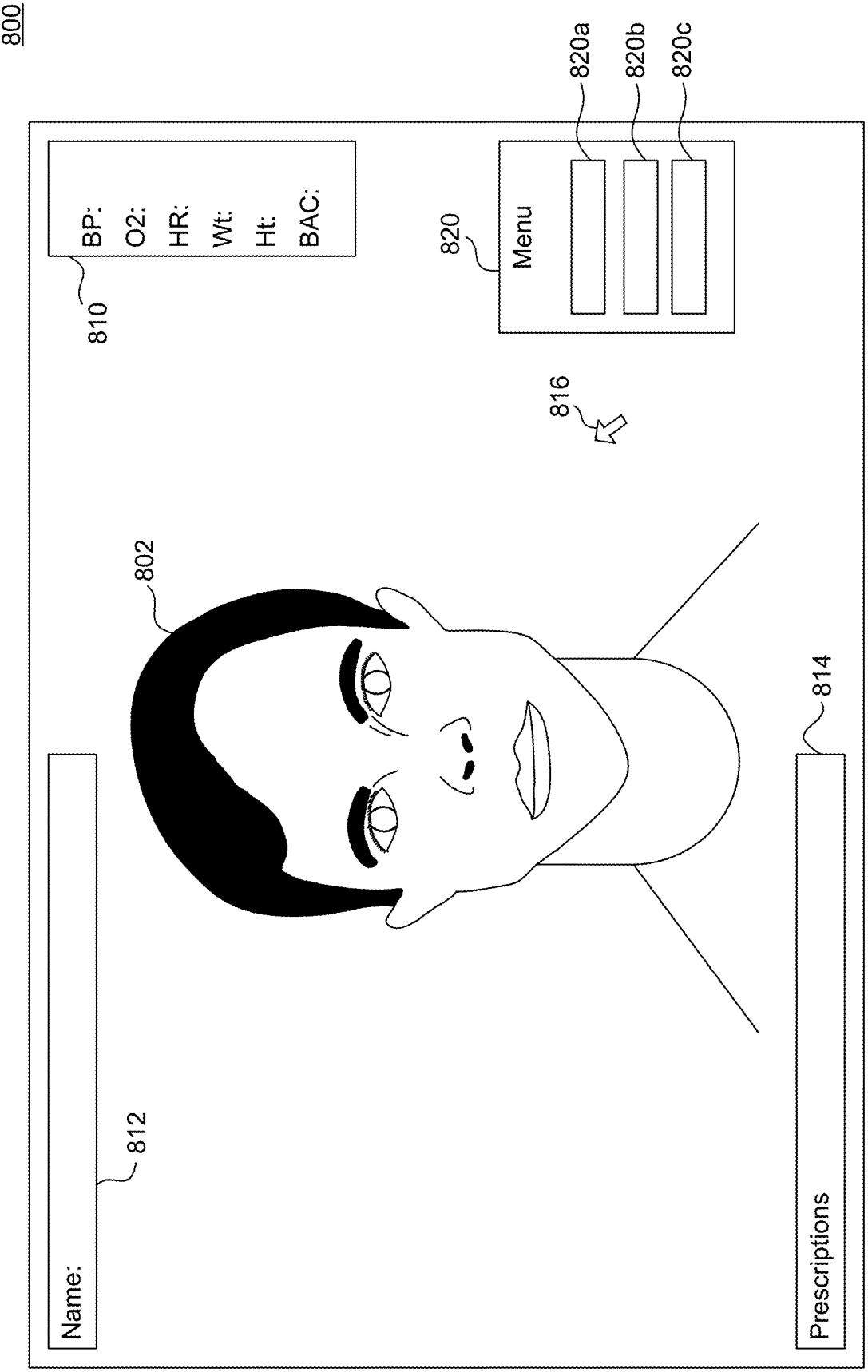
FIG. 8 illustrates a display on a physician kiosk according to exemplary embodiments of the present disclosure.

FIG. 8 illustrates an exemplary display 800 at a kiosk while it participates in a secure video call. In various embodiments, the display 800 can be either a physician kiosk or an inmate kiosk. The display 800 includes a video portion 801 displaying a real-time video of inmate or physician 802. In some embodiments, not shown in FIG. 8, display 800 includes a picture-in-picture display of the physician's own video feed in order for the physician to have certainty as to what the inmate sees on his or her corresponding inmate kiosk display.

As illustrated in FIG. 8, a plurality of displays overlay the video portion 801, including inmate identification 812, inmate vital signs 810, inmate prescriptions 814, and menu 820. In various embodiments, inmate vital signs 810 include blood pressure, oxygen saturation, heart rate, weight, height, and blood alcohol level. Regardless of whether display 800 corresponds to an inmate kiosk or a physician kiosk, inmate vital signs 810 are gathered at the medical center, remote from the physician kiosk, using medical sensors 627. Inmate identification 812 and prescriptions 814 are retrieved, illustratively, from the inmate's record stored in data storage 210.

A user, such as a physician, inmate, or medical assistant, can use a mouse or other tracking peripheral to control pointer 816. For example, a user can interact with the kiosk using menu 820. The specific options in menu 820 differ for physician kiosks relative to inmate kiosks. Using menu 820 on a physician kiosk, a physician views the medical history of the inmate stored in data storage 210; transmits instructions to the inmate or medical assistant; ends the secure video call; or controls various medical sensors located near the inmate kiosk. Using menu 820 on an inmate kiosk, an inmate or medical assistant prints an image transmitted by the physician, enters identification information, and reviews instructions provided by the physician. For example, a physician may scan an X-ray image of an inmate's hand and send the image to the inmate along with a detailed description of the image and a prognosis. The inmate or medical assistant optionally prints the image and reviews the description/prognosis on the display device of the inmate kiosk.

Exemplary Telemedicine Video Call

Figure 9:
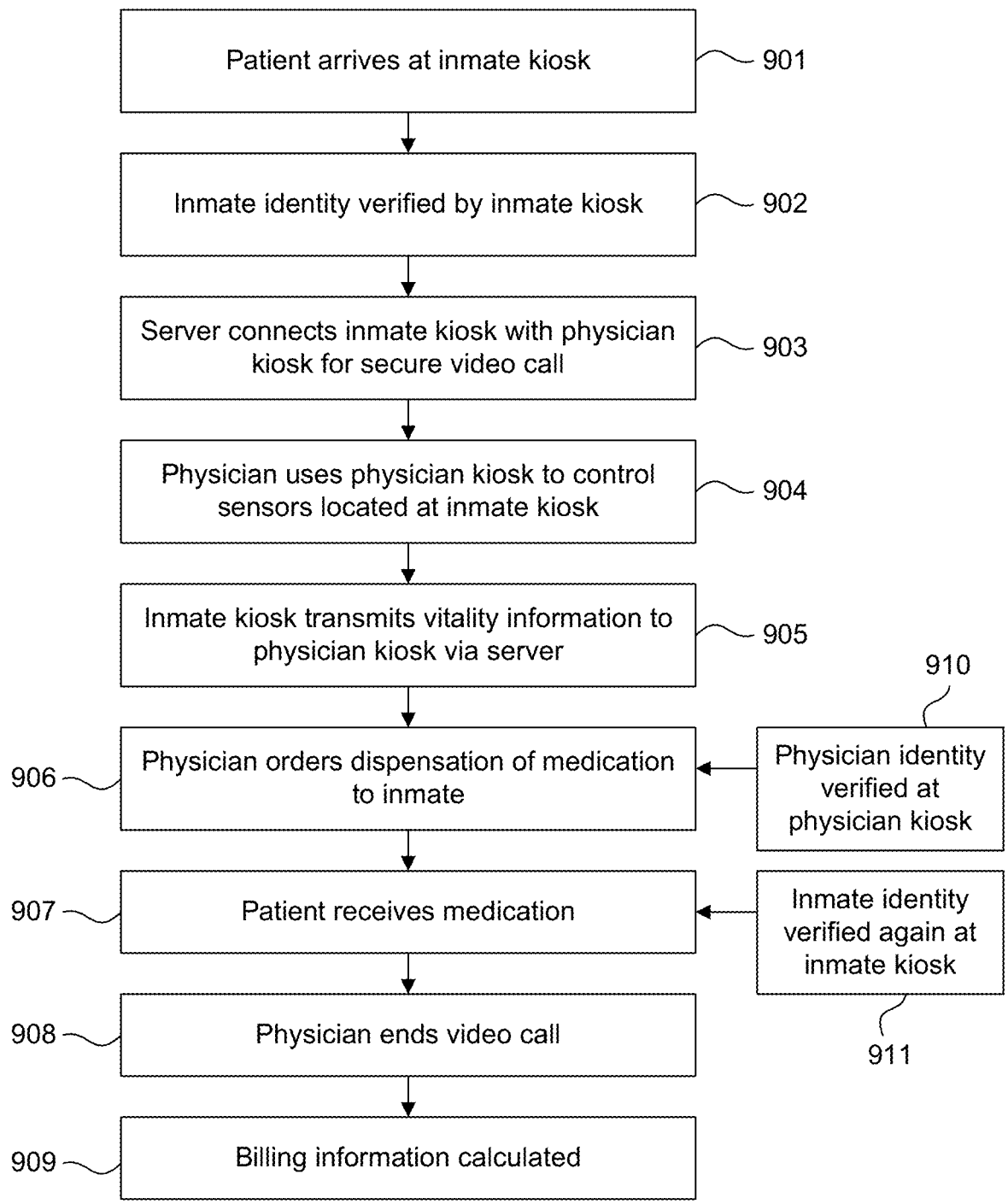
FIG. 9 illustrates an exemplary telemedicine video call between a physician and an inmate using kiosks.

FIG. 9 illustrates an exemplary method 900 for performing a telemedicine video call between a physician kiosk and an inmate kiosk using a central server. In embodiments, the physician kiosk is the exemplary physician kiosk illustrated in FIG. 7, the inmate kiosk is the exemplary inmate kiosk illustrated in FIG. 6, and the central server is the telemedicine center illustrated in FIG. 2.

After a patient arrives at an inmate kiosk in step 901, the inmate's identity is verified in step 902. The step of identifying the inmate uses, in various embodiments, a password, identification number, or biometric identification. Biometric identification includes three-dimensional facial structure identification, fingerprinting, or retina scanning, in addition to conventional biometric identification approaches.

In step 903, the inmate kiosk is connected in a video call to a physician kiosk. The connection is facilitated by the central server. In some embodiments, the inmate can be identified after the video call is connected. In further embodiments, the physician initiates the video call with the inmate, and in other embodiments, the inmate initiates the video call with the physician.

The physician and inmate proceed to conduct a medical consultation using their respective kiosks. In step 904, the physician uses a sensor controller in the physician kiosk to control sensors located at the inmate kiosk. In some embodiments, a medical assistant aids with the operation of the sensors. As described with respect to FIGS. 6-7, the sensors transmits medical data, including vital signs, wirelessly to the inmate kiosk. In step 905, the inmate kiosk, transmits the medical data to the central server, which relays the information to the physician kiosk. The data is displayed at the physician kiosk, for example as illustrated in FIG. 8.

In step 906, the physician uses the physician kiosk to order medication to be dispensed to the inmate. Prior to providing this order, the physician is identified in step 910. This identification can be performed at any point prior to the medication order and can include biometric identification, password, or a radio frequency identification (RFID) card. The order is received at the medication dispenser located at the inmate kiosk, which again verifies the inmate's identity in step 911. In step 907, the medication is dispensed to the patient. In some embodiments, the medical assistant aids with the dispensation of medication.

At the end of the consultation, the physician ends the video call using the physician kiosk in step 908. During the call 900, billable events are logged such that after the call, in step 909, a bill can be automatically calculated by the physician kiosk or by the central server and sent to the correctional facility.

Exemplary Computer Implementation

It will be apparent to persons skilled in the relevant art(s) that various elements and features of the present disclosure, as described herein, can be implemented in hardware using analog and/or digital circuits, in software, through the execution of computer instructions by one or more general purpose or special-purpose processors, or as a combination of hardware and software.

Figure 10:
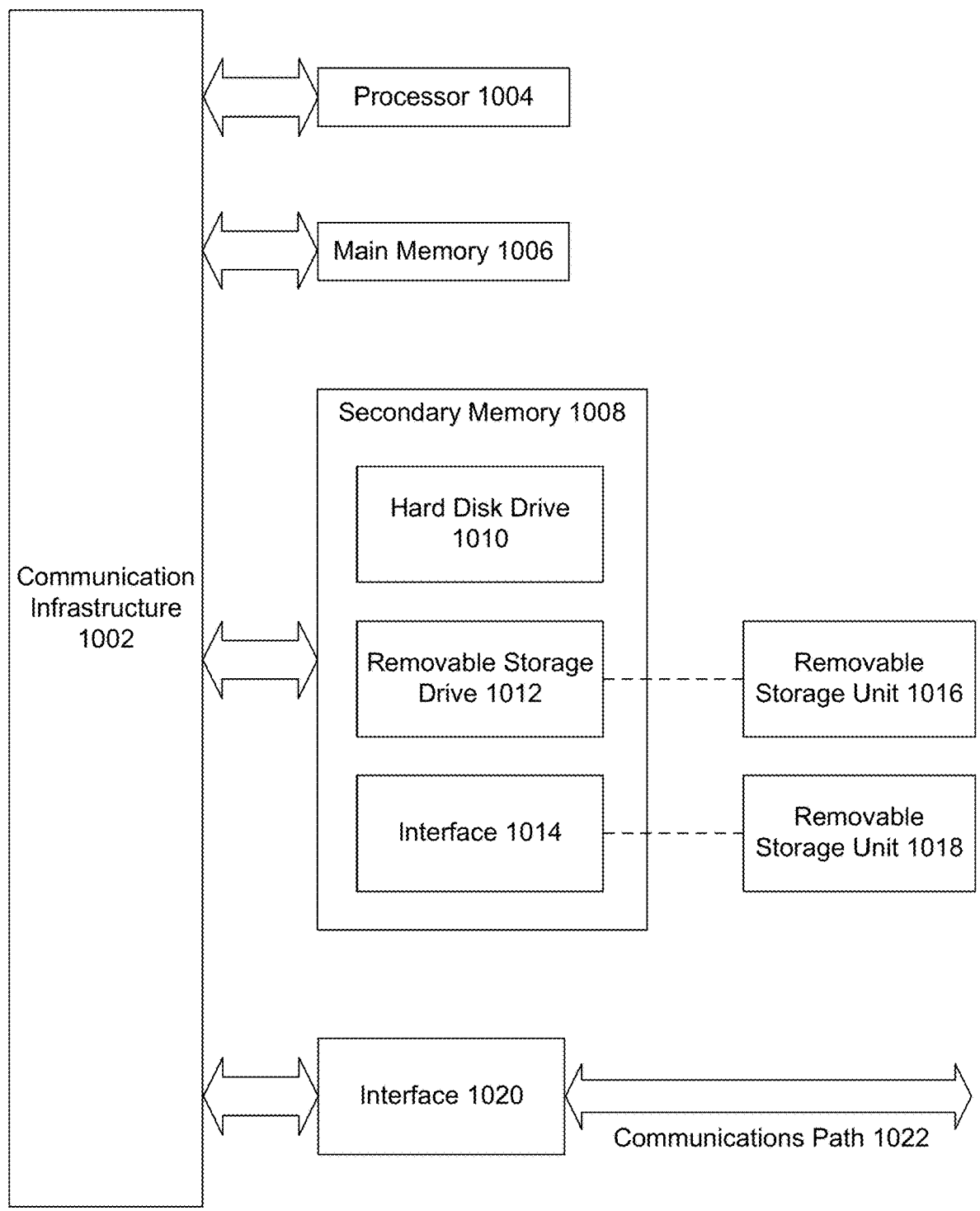
FIG. 10 illustrates a computer system, according to exemplary embodiments of the present disclosure.

The following description of a general purpose computer system is provided for the sake of completeness. Embodiments of the present disclosure can be implemented in hardware, or as a combination of software and hardware. Consequently, embodiments of the disclosure may be implemented in the environment of a computer system or other processing system. An example of such a computer system 1000 is shown in FIG. 10. One or more of the modules depicted in the previous figures can be at least partially implemented on one or more distinct computer systems 1000.

Computer system 1000 includes one or more processors, such as processor 1004.

Processor 1004 can be a special purpose or a general purpose digital signal processor. Processor 1004 is connected to a communication infrastructure 1002 (for example, a bus or network). Various software implementations are described in terms of this exemplary computer system. After reading this description, it will become apparent to a person skilled in the relevant art(s) how to implement the disclosure using other computer systems and/or computer architectures.

Computer system 1000 also includes a main memory 1006, preferably random access memory (RAM), and may also include a secondary memory 1008. Secondary memory 1008 may include, for example, a hard disk drive 1010 and/or a removable storage drive 1012, representing a floppy disk drive, a magnetic tape drive, an optical disk drive, or the like. Removable storage drive 1012 reads from and/or writes to a removable storage unit 1016 in a well-known manner. Removable storage unit 1016 represents a floppy disk, magnetic tape, optical disk, or the like, which is read by and written to by removable storage drive 1012. As will be appreciated by persons skilled in the relevant art(s), removable storage unit 1016 includes a computer usable storage medium having stored therein computer software and/or data.

In alternative implementations, secondary memory 1008 may include other similar means for allowing computer programs or other instructions to be loaded into computer system 1000. Such means may include, for example, a removable storage unit 1018 and an interface 1014. Examples of such means may include a program cartridge and cartridge interface (such as that found in video game devices), a removable memory chip (such as an EPROM, or PROM) and associated socket, a thumb drive and USB port, and other removable storage units 1018 and interfaces 1014 which allow software and data to be transferred from removable storage unit 1018 to computer system 1000.

Computer system 1000 may also include a communications interface 1020. Communications interface 1020 allows software and data to be transferred between computer system 1000 and external devices. Examples of communications interface 1020 may include a modem, a network interface (such as an Ethernet card), a communications port, a PCMCIA slot and card, etc. Software and data transferred via communications interface 1020 are in the form of signals which may be electronic, electromagnetic, optical, or other signals capable of being received by communications interface 1020. These signals are provided to communications interface 1020 via a communications path 1022. Communications path 1022 carries signals and may be implemented using wire or cable, fiber optics, a phone line, a cellular phone link, an RF link and other communications channels.

As used herein, the terms "computer program medium" and "computer readable medium" are used to generally refer to tangible storage media such as removable storage units 1016 and 1018 or a hard disk installed in hard disk drive 1010. These computer program products are means for providing software to computer system 1000.

Computer programs (also called computer control logic) are stored in main memory 1006 and/or secondary memory 1008. Computer programs may also be received via communications interface 1020. Such computer programs, when executed, enable the computer system 1000 to implement the present disclosure as discussed herein. In particular, the computer programs, when executed, enable processor 1004 to implement the processes of the present disclosure, such as any of the methods described herein. Accordingly, such computer programs represent controllers of the computer system 1000. Where the disclosure is implemented using software, the software may be stored in a computer program product and loaded into computer system 1000 using removable storage drive 1012, interface 1014, or communications interface 1020.

In another embodiment, features of the disclosure are implemented primarily in hardware using, for example, hardware components such as application-specific integrated circuits (ASICs) and gate arrays. Implementation of a hardware state machine so as to perform the functions described herein will also be apparent to persons skilled in the relevant art(s).

CONCLUSION

It is to be appreciated that the Detailed Description section, and not the Abstract section, is intended to be used to interpret the claims. The Abstract section may set forth one or more, but not all exemplary embodiments, and thus, is not intended to limit the disclosure and the appended claims in any way.

The invention has been described above with the aid of functional building blocks illustrating the implementation of specified functions and relationships thereof. The boundaries of these functional building blocks have been arbitrarily defined herein for the convenience of the description. Alternate boundaries may be defined so long as the specified functions and relationships thereof are appropriately performed.

It will be apparent to those skilled in the relevant art(s) that various changes in form and detail can be made therein without departing from the spirit and scope of the disclosure. Thus, the invention should not be limited by any of the above-described exemplary embodiments, but should be defined only in accordance with the following claims and their equivalents.

What is claimed is:

1. A patient kiosk for conducting a remote medical examination of an inmate in a prison, the patient kiosk comprising:
   an image capture device;
   a display device;
   a communication device configured to communicate with a server;
   a plurality of sensors including a biometric sensor and one or more vitality sensors;
   a wireless communication device configured to communicate with the plurality of sensors;
   one or more processors and/or circuits configured to:
     receive biometric information from the inmate via the biometric sensor;
     communicate with a central server to verify an identity of the inmate and a permission of the inmate to conduct a secure video call with a physician based on the received biometric information;

establish the secure video call connection with a physician kiosk via the communication device in response to verifying the identity and the permission of the inmate;

receive incoming video call data from the server via the communication device;

output the received video call data to the display device;

receive outgoing video call data from the image capture device;

transmit the outgoing video call data to the server via the communication device;

receive incoming sensor data from the wireless communication device;

receive vitality information from the inmate via the one or more vitality sensors; and securely transmit the vitality information to the server via the communication device; and a medication dispensing station configured to:

receive prescription data, including an inmate identity; and dispense the medication to the inmate.

2. The patient kiosk of claim 1, wherein the medication dispensing station is further configured to:

determine an inmate identity associated with an inmate interacting with the patient kiosk;

determine that the inmate identity associated with the inmate interacting with the patient kiosk matches the received inmate identity;

dispense the medication to the inmate interacting with the patient kiosk.

3. The patient kiosk of claim 2, wherein the medication dispensing station is further configured to receive an authorization signal from the server prior to dispensing the medication to the inmate.

4. The patient kiosk of claim 2, wherein the inmate identity is determined using three-dimensional facial architecture recognition.

5. The patient kiosk of claim 1, wherein the plurality of sensors comprises at least one of a temperature sensor, a blood pressure monitor, an oxygen sensor, or a pulse rate monitor.

6. The patient kiosk of claim 1, wherein the plurality of sensors comprises at least one of a DNA collector, a device for blood and urine analysis, a stethoscope, a Breathalyzer, or a weight scale.

7. The patient kiosk of claim 1, wherein the one or more processors and/or circuits are further configured to:

receive medical imaging data from the server; and output the medical imaging data to the display device.

8. The patient kiosk of claim 7, wherein the medical imaging data comprises a digital image and text associated with the digital image; and wherein the display device is configured to display the text associated with the digital image as a scrolling data feed over the digital image.

9. The patient kiosk of claim 1, further comprising a cardiac arrest unit including at least one of an automatic cardiopulmonary resuscitation machine or an automated external defibrillator.

10. The patient kiosk of claim 1, wherein the one or more processors and/or circuits are further configured to:

establish a group video call connection with a plurality of kiosks, including a physician kiosk;

receive incoming group video call data from the server, the incoming group video call data originating from the plurality of kiosks;

output the received group video call data to the display device;

receive outgoing video call data from the image capture device; and transmit the outgoing video call data to the server, the outgoing video call data destined for the plurality of kiosks.

11. A physician kiosk for conducting a remote medical examination of an inmate in a prison, comprising:

an image capture device;

a display device;

a communication device configured to communicate with a server;

a sensor control device configured to control one or more remote sensors located at a patient kiosk within a prison facility; and one or more processors and/or circuits configured to:

establish a video call connection with the patient kiosk via the communication device;

receive incoming video call data from the server via the communication device;

output the received video call data to the display device;

receive outgoing video call data from the image capture device;

transmit the outgoing video call data to the server via the communication device;

transmit sensor control signals to the patient kiosk configured to control the one or more remote sensors to gather data from the inmate;

receive incoming sensor data from the server via the communication device in response to the sensor control signals; and output the incoming sensor data to the display device; and a medication dispensing controller configured to:

receive medication dispensing instructions and authorization from a physician; and transmit the medication dispensing instructions to the patient kiosk and the dispensing authorization to the server via the communication device for causing the patient kiosk to dispense medication to the inmate according to dispensing instructions.

12. The physician kiosk of claim 11, wherein the medication dispensing controller is further configured to authenticate an identity of the physician.

13. The physician kiosk of claim 11, wherein the one or more remote sensors comprises one or more of a wand camera probe or a stethoscope.

14. The physician kiosk of claim 11, wherein the one or more processors and/or circuits are further configured to automatically generate an invoice to an institution for services performed by the physician.

* * * * *